United States Patent [19]

Halpern et al.

[11] 4,201,705

[45] * May 6, 1980

[54] INTUMESCENT FLAME RETARDANT POLYOLEFIN COMPOSITIONS

[75] Inventors: Yuval Halpern, Skokie, Ill.; Clifton T. Fleenor, Parkersburg, W. Va.

[73] Assignee: Borg-Warner Corporation, Chicago, Ill.

[*] Notice: The portion of the term of this patent subsequent to May 15, 1996, has been disclaimed.

[21] Appl. No.: 937,343

[22] Filed: Aug. 28, 1978

[51] Int. Cl.$^2$ ................................................ C08J 9/00
[52] U.S. Cl. ...................... 260/45.8 NT; 260/927 R; 521/90; 521/129; 521/143; 521/144; 521/907; 544/195

[58] Field of Search ................... 260/45.8 NT, 927 R; 521/90, 143, 144, 907

[56] References Cited

U.S. PATENT DOCUMENTS

| | | | |
|---|---|---|---|
| 3,090,799 | 5/1963 | Wahl | 260/927 R |
| 3,192,243 | 6/1965 | Gagliani | 260/927 R |

*Primary Examiner*—Morton Foelak
*Attorney, Agent, or Firm*—Richard J. Schlott

[57] ABSTRACT

Polyolefin compositions comprising a polyolefin and a flame retarding amount of the pentate salt of an amino-s-triazine are intumescent and self-extinguishing and non-dripping.

7 Claims, No Drawings

INTUMESCENT FLAME RETARDANT POLYOLEFIN COMPOSITIONS

BACKGROUND OF THE INVENTION

This invention relates to flame retardant polyolefin compositions. More particularly, this invention relates to flame retardant polyolefin compositions comprising polyolefin and a flame retarding amount of the pentate salt of an amino-s-triazine and to a method for rendering polyolefins flame retardant.

Polyolefins are difficult to render flame retardant. A number of halogen-containing flame retardants are known which, when compounded with polyolefins, provide non-burning compositions, i.e. materials which do not propagate flame. However, polyolefins such as polypropylene have a tendency toward dripping flaming drops which is quite difficult to overcome, and such non-burning compositions generally are not capable of being made fully self-extinguishing.

An alternative approach is to incorporate charforming additives which, in the presence of flame, form a thick, non-flammable insulating barrier to protect the substrate polymer. One such intumescent or char-forming system, disclosed in U.S. Pat. No. 3,936,416, employs a combination of melamine pyrophosphate and a polyol. This additive combination is effective in providing a non-burning, non-dripping polypropylene composition. Preparation and compounding with these materials can be difficult. During preparation, the additive combination must be degassed in order to avoid foaming during the compounding with polypropylene and/or in subsequent molding operations. In addition, the additive as obtained has a substantial tan or brown color which imparts an undesirable hue to the polypropylene composition, and the additive is obtained as a hard, solid mass which is pulverized with some difficulty for compounding.

An additive composition which has little or no foaming tendency at processing temperatures and which could be readily produced in usable form and without undesirable darker coloration would be a substantial advance over the presently available intumescent flame retardant additives for polyolefins.

SUMMARY OF THE INVENTION

The pentate salts of amino-s-triazines are effective intumescent flame retardant additives for polyolefins, providing compositions that are self-extinguishing, intumescent and non-dripping. The additives are dry, white, powdery solids and are readily compounded with polyolefins to provide compositions which have excellent color and which are readily processed without apparent foaming or decomposition during molding.

DETAILED DESCRIPTION OF THE INVENTION

The flame retardant polyolefin compositions of this invention comprise a olefin homopolymer or copolymer and a flame retarding amount of a pentate salt of an amino-s-triazine.

The polyolefins useful for the purposes of this invention are polymers of alpha-olefins, such as ethylene, propylene, isobutylene, butene-1 and the like, and copolymers thereof. Homopolymers and copolymers of polyolefins are commercially available in a wide range of molecular weights and densities, and in general all will be useful for forming the flame retardant compositions of this invention.

The pentate salts of amino-s-triazines useful for the purposes of this invention are pentaerythritol diphosphate salts (pentates) having the following structure:

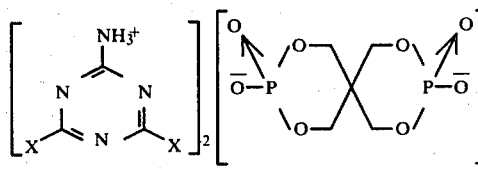

wherein x may be —NH$_2$ or —OH, and include melammonium pentate, (x=—NH$_2$), the pentate salt of ammelide (x=OH), and mixtures thereof.

The pentate salts of amino-s-triazines are readily prepared by first hydrolyzing a pentate compound such as dichloropentate to provide the free acid, then reacting that product with the requisite amount of the amino-s-triazine to form the sparingly soluble salt. For example, the dichloropentate is first hydrolyzed by warming with aqueous alkali. This product is then added to a warm aqueous solution of the amino-s-triazine containing sufficient mineral acid to dissolve the triazine. The sparingly soluble pentate salt precipitates from the solution as a fine powder or crystalline compound. As an alternative, an acid acceptor such as a tertiary alkyl amine may be employed in place of the alkali to promote the hydrolysis reaction. As a third alternative, the amino-s-triazine may be added to the aqueous mixture prior to hydrolysis, whereupon the pentate salt is formed and precipitates as the hydrolysis proceeds. The preparation of pentate salts of amino-s-triazines is more fully described in my copending U.S. patent application Ser. No. 937,341, filed Aug. 28, 1978, now U.S. Pat. No. 4,154,930 issued May 15, 1979.

The amount of flame retardant pentate salt employed will be from about 20 to about 50 wt. percent of the total composition. The pentate salts may be employed alone or together with a polyol such as for example pentaerythritol, dipentaerythritol or tripentaerythritol to aid in forming char. The compounding of the polyolefin with the flame retardant pentate salt may be carried out in any of the conventional compounding processes including Banbury mixing melt extrusion and the like.

The following examples are provided to illustrate the practice of the invention.

The following formulations were prepared; all proportions are in parts by weight.

Table I

| Example Numbers | 1 | 2 | 3 | 4 | 5 | 6 | 7 | 8 | 9 |
| --- | --- | --- | --- | --- | --- | --- | --- | --- | --- |
| Polypropylene | 100[1] | 100[1] | 100[2] | 100[2] | 100[2] | — | — | — | — |
| Propylene Copolymer[1] | — | — | — | — | — | 100 | 100 | — | — |
| Polyethylene | — | — | — | — | — | — | — | 100 | 100 |
| Melammonium Pentate | — | 25 | 30 | 25 | 25 | 25 | — | 40 | 100 |
| Pentaerythritol | — | — | — | 5 | — | — | — | — | — |
| Dipentaerythritol | — | 5 | — | — | 5 | 5 | — | — | — |

Table I-continued

| Example Numbers | 1 | 2 | 3 | 4 | 5 | 6 | 7 | 8 | 9 |
|---|---|---|---|---|---|---|---|---|---|
| DSTDP[3] | 0.2 | 0.2 | — | — | — | 0.2 | 0.2 | — | — |
| Irganox 1010[3] | 0.1 | 0.1 | — | — | — | 0.1 | 0.1 | — | — |
| BHT[3] | 0.05 | 0.05 | — | — | — | 0.05 | 0.05 | — | — |
| Calcium Stearate | 0.05 | 0.05 | — | — | — | 0.05 | 0.05 | — | — |
| FR Additive, wt.% | — | 23 | 23 | 23 | 23 | 23 | — | 28.6 | 50 |

Notes:
[1]Polypropylene homopolymer, obtained as Profax 6501 from Hercules Chemical Co. Propylene-ethylene copolymer, obtained as Profax 8501 from Hercules Chemical Co.
[2]Polypropylene homopolymer obtained as Profax 6523 from Hercules Chemical Co.
[3]DSTDP = distearyl thiodipropionate; Irganox 1010 = antioxidant from Ciba-Geigy Corp; BHT = butylated hydroxytoluene.

The compounding was carried out by first dry-mixing the additive components with the powdered polypropylene then extruding the mixture using a 28 mm twin screw extruder with barrel temperatures of 360°–370° F., a die temperature of 385°–400° F.and screw speed of 27 t rpm. The extrudate was chopped into pellets. The resin compositions were then injection molded on a 3 oz Van Dorn, employing a stock temperature of 420° F., to form tensile bars, discs and flammability test bars. The test data for the various compositions are summarized in Table II.

TABLE II

| | Flammability Properties, UL 94 Test, ⅛" Bars | | | | | | | | |
|---|---|---|---|---|---|---|---|---|---|
| Ex. No. | 1 | 2 | 3 | 4 | 5 | 6 | 7 | 8 | 9 |
| Rating | NSE | V-O | V-O | V-O | V-O | NSE | NSE | NSE | V-O |
| Ave. burn time, sec. | — | 1.0 | 1.6 | 2.5 | 2.9 | — | — | — | 3.4 |
| Max. burn time, sec. | 30+ | 1.0 | 5 | 7 | 9 | 30+ | 30+ | 30+ | 8 |

It will be apparent that a propylene homopolymer is made flame retardant by the addition of as little as 23 wt.% melammonium pentate (compare Example 1 with Examples 2 and 3). Polyethylene requires substantially higher levels of the intumescent flame retardant additive, as shown by Examples 8 and 9, wherein the composition of Example 9 containing 50 wt.% of the additive is self-extinguishing, V-O rating, while the composition containing 28.6 wt.% (Example 8), is rated NSE. Both exhibited char-formation and intumescent behavior. The copolymer material of Example 6 was not rendered self-extinguishing by the addition of 23 wt.% additive, (Example 7) however this composition also was intumescent, forming an excellent structured char; at higher levels of additive the copolymer composition will be self-extinguishing.

EXAMPLE 10

The pentate salt of ammelide was prepared and compounded with polypropylene to provide a composition containing 30 parts by wt. (23 wt.%) of the pentate salt. Molded bars (⅛") were tested according to UL 94 test. The composition was rated self-extinguishing, V-O with a maximum burn time of 8 sec. and an average burn time of 2 sec. The composition was intumescent, forming an excellent structured char.

Minor amounts of a polyol such as for example pentaerythritol, dipentaerythritol, tripentaerythritol or the like may be included in the composition to assist in char forming, as shown in Examples 2 and 4–6.

In a comparative test, polystyrene was compounded with melammonium pentate to provide a composition containing 28.6 wt.% additive. Test bars were molded and submitted to UL-94 flame test. All specimens burned completely after the flame source was removed, without forming a char.

Surprisingly, the compositions of this invention produce for less smoke when burned than do conventional flame retardant grades of polypropylene compounded with halogenated flame retardants. The composition of Example 3, when burned in a UL Smoke Chamber test, gave a smoke density rating of Dm=121. A commercial flame retardant polypropylene containing a halogenated flame retardant and antimony oxide gave a smoke density rating of Dm=293 in the same test. The compositions of this invention thus have a further and unexpected advantage over conventional flame retardant compositions comprising halogenated flame retardants.

The invention will thus be seen to be compositions comprising a polyolefin selected from the group polypropylene, polyethylene and copolymers of ethylene and propylene and a flame-retarding amount of the pentate salt of an amino-s-triazine, said salt being selected from the group melammonium pentate, the pentate salt of ammelide and mixtures thereof, wherein the amount of said salt will be from about 20 to about 50 percent by weight of the total composition, and a method for rendering polyolefins intumescent and self-extinguishing.

Further modifications including the use of dyes, pigments, fillers, stabilizers and the like will be apparent to those skilled in the art, and such additives and modifications may be made without departing from the spirit and scope of the invention, which is defined solely by the following claims.

I claim:

1. Polyolefin compositions comprising a polyolefin and a flame retarding amount of an intumescent additive selected from the group consisting of melammonium pentate, the pentate salt of ammelide, the mixtures thereof.

2. The composition of claim 1 wherein the intumescent additive is present in from about 20 to about 50 percent by weight of the total composition.

3. The composition of claim 1 wherein the polyolefin is selected from the group consisting of polypropylene, polyethylene and copolymers thereof.

4. The composition of claim 1 wherein said additive is melammonium pentate.

5. The composition of claim 1 wherein said additive is the pentate salt of ammelide.

6. A method for rendering polyolefins intumescent and self-extinguishing consisting of compounding therewith from about 20 to about 50 percent by weight based on final composition of an additive selected from the group consisting of melammonium pentate, the pentate salt of ammelide and mixtures thereof.

7. Polyolefin compositions comprising a polyolefin and from about 20 to about 50 percent by weight, based on final composition, of the substantially water-insoluble product produced by heating under reflux conditions a mixture of an amino-s-triazine selected from the group consisting of melamine, ammelide and mixtures thereof, and a dichloropentate, in a molar ratio of about 2:1 in the presence of water.

* * * * *

UNITED STATES PATENT AND TRADEMARK OFFICE
CERTIFICATE OF CORRECTION

PATENT NO. : 4,201,705
DATED : May 6, 1980
INVENTOR(S) : Yuval Halpern

It is certified that error appears in the above—identified patent and that said Letters Patent is hereby corrected as shown below:

On The Title Page Item (75), delete "Clifton T. Fleenor, Parkersburg, W. Va. --.

Signed and Sealed this

Twelfth Day of May 1981

[SEAL]

Attest:

RENE D. TEGTMEYER

Attesting Officer     Acting Commissioner of Patents and Trademarks